(12) United States Patent
Chassot et al.

(10) Patent No.: US 7,491,244 B2
(45) Date of Patent: Feb. 17, 2009

(54) OXIDIZING HAIR COLORING AGENTS CONTAINING M-AMINOPHENOL DERIVATIVES

(75) Inventors: Laurent Chassot, Praroman (CH); Hans-Jürgen Braun, Ueberstorf (CH)

(73) Assignee: The Procter & Gamble Company, Cincinnati, OH (US)

( * ) Notice: Subject to any disclaimer, the term of this patent is extended or adjusted under 35 U.S.C. 154(b) by 121 days.

(21) Appl. No.: 11/503,320

(22) Filed: Aug. 11, 2006

(65) Prior Publication Data

US 2007/0033745 A1 Feb. 15, 2007

(30) Foreign Application Priority Data

Aug. 12, 2005 (EP) .................. 05017565

(51) Int. Cl.
*A61Q 5/10* (2006.01)
(52) U.S. Cl. .................. 8/405; 8/406; 8/408; 8/410; 8/411; 8/421; 8/435
(58) Field of Classification Search ............. 8/405, 8/406, 408, 410, 411, 421, 435
See application file for complete search history.

(56) References Cited

U.S. PATENT DOCUMENTS

| 4,003,699 | A | * | 1/1977 | Rose et al. ............ 8/409 |
| 4,575,377 | A | | 3/1986 | Rose et al. |
| 6,409,995 | B1 | | 6/2002 | Habeck et al. |

FOREIGN PATENT DOCUMENTS

DE 19606644 A1 8/1997

GB 1486576 A 9/1977

OTHER PUBLICATIONS

STIC Search Report dated Mar. 10, 2008.*
International Search Report for PCT/IB2006/052743, Jan. 12, 2007 (2 pages).
Advanced Organic Chemistry—Reactions, Mechanisms and Structure (Jerry March, 5th Edition (2001), pp. 368-375.

* cited by examiner

*Primary Examiner*—Eisa B Elhilo
(74) *Attorney, Agent, or Firm*—Melissa Krasovec; Marianne Dressman; Tara M. Rosnell

(57) ABSTRACT

The object of the present patent application are agents for the oxidative coloring of keratin fibers, particularly hair, based on a developer substance-coupler substance combination, characterized in that they contain at least one meta-aminophenol derivative of general formula (I)

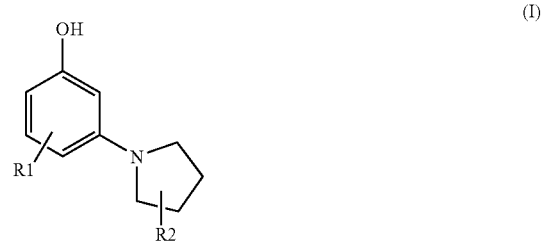

wherein
R1 denotes hydrogen, a C1-C6 alkyl group, a C2-C4 hydroxyalkyl group, a C2-C4 dihydroxyalkyl group, a C1-C4 alkoxy group or a halogen atom; and R2 denotes hydrogen, a hydroxy group, a carboxylic group, an aminocarbonyl group or a hydroxymethyl group.

8 Claims, No Drawings

OXIDIZING HAIR COLORING AGENTS CONTAINING M-AMINOPHENOL DERIVATIVES

FIELD OF THE INVENTION

The present invention relates to agents for oxidative coloring of keratin fibers, particularly human hair, based on a developer substance/coupler substance combination which contains a meta-aminophenol where the amino group is part of a 5 membered heterocyclic ring.

BACKGROUND OF THE INVENTION

In the field of dyeing keratin fibers, in particular hair coloring, oxidation dyes have achieved significant importance. The coloration arises here as a result of the reaction of certain developer substances with certain coupler substances in the presence of a suitable oxidizing agent. The developer substances used here are, in particular, 2,5-diaminotoluene, 2,5-diaminophenylethyl alcohol, p-aminophenol and 1,4-diaminobenzene, while examples of coupler substances are resorcinol, 4-chlororesorcinol, 1-naphthol, 3-aminophenol and derivatives of m-phenylenediamine.

Besides dyeing to the desired intensity, numerous additional requirements are placed on oxidation dyes which are used for coloring human hair. For example, the dyes must be acceptable from a toxicological and dermatological point of view and the hair colorations achieved must have good light fastness, permanent wave fastness, acid fastness, and rubbing fastness. However, in any case, such colorations must remain stable over a period of at least 4 to 6 weeks without being affected by light, rubbing, and chemical agents. Furthermore, it is required that, by combining suitable developer substances and coupler substances, a broad palette of different color nuances can be produced.

For providing a natural coloration of the hair 1,3-dihydroxybenzene has been used in combination with p-phenylendiamine derivatives.

German Patent No. DE-A 32 33 541 suggests the use of substituted 1,3-dihydroxybenzene as couplers, nevertheless it is not possible to satisfy the above mentioned requirements in all aspects. Therefore there is a need for new couplers which provide natural colors for use in oxidative hair dyeing composition.

SUMMARY OF THE INVENTION

In this regard, we have now found that meta-aminophenol derivatives of general formula (I) meet the requirements placed on coupler components to an unusually high degree. Thus, by use of such coupler components together with known developer components, natural color shades are obtained which are unusually resistant to light and washing.

DETAILED DESCRIPTION OF THE INVENTION

The present invention therefore relates to agents for the oxidative coloring of keratin fibers, for example wool, furs, feathers, or hair, particularly human hair, based on a developer substance/coupler substance combination containing as a coupler a meta-aminophenol derivative of the general formula (I) or its physiologically compatible, water-soluble salt,

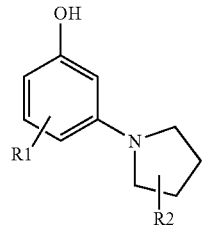

(I)

wherein
R1 denotes hydrogen, a C1-C6 alkyl group, C2-C4 hydroxyalkyl group, a C3-C4 dihydroxyalkyl group, a C1-C4 alkoxy group, or a halogen atom; and
R2 denotes hydrogen, a hydroxy group, a carboxylic group, an aminocarbonyl group, or a hydroxymethyl group.
Suitable compounds of formula (I) are, for example:
3-(1-pyrrolidinyl)phenol, 2-chloro-3-(1-pyrrolidinyl)phenol, 2-fluoro-3-(1-pyrrolidinyl)phenol, 2-methoxy-3-(1-pyrrolidinyl)phenol, 4-chloro-3-(1-pyrrolidinyl)phenol, 4-fluoro-3-(1-pyrrolidinyl)phenol, 4-methoxy-3-(1-pyrrolidinyl)phenol, 5-chloro-3-(1-pyrrolidinyl)phenol, 5-fluoro-3-(1-pyrrolidinyl)phenol, 5-methoxy-3-(1-pyrrolidinyl)phenol, 6-chloro-3-(1-pyrrolidinyl)phenol, 6-fluoro-3-(1-pyrrolidinyl)phenol, 6-methoxy-3-(1-pyrrolidinyl)phenol, 2-chloro-3-(2-carboxylic acid-1-pyrrolidinyl)phenol,
2-chloro-3-(2-carboxamide-1-pyrrolidinyl)phenol, 2-chloro-3-(2-hydroxy-1-pyrrolidinyl)phenol,
2-chloro-3-(2-hydroxymethyl-1-pyrrolidinyl)phenol,
2-chloro-3-(2-methoxymethyl-1-pyrrolidinyl)phenol,
2-chloro-3-(3-carboxylic acid-1-pyrrolidinyl)phenol,
2-chloro-3-(3-carboxamide-1-pyrrolidinyl)phenol,
2-chloro-3-(3-hydroxy-1-pyrrolidinyl)phenol, 2-chloro-3-(3-hydroxymethyl-1-pyrrolidinyl)phenol, 2-chloro-3-(3-methoxymethyl-1-pyrrolidinyl)phenol, 2-fluoro-3-(2-carboxylic acid-1-pyrrolidinyl)phenol,
2-fluoro-3-(2-carboxamide-1-pyrrolidinyl)phenol, 2-fluoro-3-(2-hydroxy-1-pyrrolidinyl)phenol,
2-fluoro-3-(2-hydroxymethyl-1-pyrrolidinyl)phenol,
2-fluoro-3-(2-methoxymethyl-1-pyrrolidinyl)phenol,
2-fluoro-3-(3-carboxylic acid-1-pyrrolidinyl)phenol,
2-fluoro-3-(3-carboxamide-1-pyrrolidinyl)phenol,
2-fluoro-3-(3-hydroxy-1-pyrrolidinyl)phenol, 2-fluoro-3-(3-hydroxymethyl-1-pyrrolidinyl)phenol, 2-fluoro-3-(3-methoxymethyl-1-pyrrolidinyl)phenol,
2-methoxy-3-(2-carboxylic acid-1-pyrrolidinyl)phenol, 2-methoxy-3-(2-carboxamide-1-pyrrolidinyl)phenol, 2-methoxy-3-(2-hydroxy-1-pyrrolidinyl)-phenol, 2-methoxy-3-(2-hydroxymethyl-1-pyrrolidinyl)phenol, 2-methoxy-3-(2-methoxymethyl-1-pyrrolidinyl)phenol, 2-methoxy-3-(3-carboxylic acid-1-pyrrolidinyl)phenol, 2-methoxy-3-(3-carboxamide-1-pyrrolidinyl)phenol, 2-methoxy-3-(3-hydroxy-1-pyrrolidinyl)phenol, 2-methoxy-3-(3-hydroxy-methyl-1-pyrrolidinyl)phenol, 2-methoxy-3-(3-methoxymethyl-1-pyrrolidinyl)phenol, 4-chloro-3-(2-carboxylic acid-1-pyrrolidinyl)phenol,
4-chloro-3-(2-carboxamide-1-pyrrolidinyl)phenol, 4-chloro-3-(2-hydroxy-1-pyrrolidinyl)phenol,
4-chloro-3-(2-hydroxymethyl-1-pyrrolidinyl)phenol,
4-chloro-3-(2-methoxymethyl-1-pyrrolidinyl)phenol,
4-chloro-3-(3-carboxylic acid-1-pyrrolidinyl)phenol,
4-chloro-3-(3-carboxamide-1-pyrrolidinyl)phenol, 4-chloro-3-(3-hydroxy-1-pyrrolidinyl)phenol, 4-chloro-3-(3-hydroxymethyl-1-pyrrolidinyl)phenol, 4-chloro-3-(3-methoxymethyl-1-pyrrolidinyl)phenol, 4-fluoro-3-(2-carboxylic acid-1-pyrrolidinyl)phenol, 4-fluoro-3-(2-carboxamide-1-pyrrolidinyl)phenol, 4-fluoro-3-(2-hydroxy-1-pyrrolidinyl)phenol, 4-fluoro-3-(2-hydroxymethyl-1-pyrrolidinyl)phenol, 4-fluoro-3-(2-methoxymethyl-1-pyrrolidinyl)phenol,
   4-fluoro-3-(3-carboxylic acid-1-pyrrolidinyl)phenol,
   4-fluoro-3-(3-carboxamide-1-pyrrolidinyl)phenol,
   4-fluoro-3-(3-hydroxy-1-pyrrolidinyl)phenol, 4-fluoro-3-(3-hydroxymethyl-1-pyrrolidinyl)phenol, 4-fluoro-3-(3-methoxymethyl-1-pyrrolidinyl)phenol, 4-methoxy-3-(2-carboxylic acid-1-pyrrolidinyl)phenol,
   4-methoxy-3-(2-carboxamide-1-pyrrolidinyl)phenol,
   4-methoxy-3-(2-hydroxy-1-pyrrolidinyl)-phenol, 4-methoxy-3-(2-hydroxymethyl-1-pyrrolidinyl)phenol, 4-methoxy-3-(2-methoxymethyl-1-pyrrolidinyl)phenol, 4-methoxy-3-(3-carboxylic acid-1-pyrrolidinyl)phenol, 4-methoxy-3-(3-carboxamide-1-pyrrolidinyl)phenol, 4-methoxy-3-(3-hydroxy-1-pyrrolidinyl)phenol, 4-methoxy-3-(3-hydroxy-methyl-1-pyrrolidinyl)phenol, 4-methoxy-3-(3-methoxymethyl-1-pyrrolidinyl)phenol,
   5-chloro-3-(2-carboxylic acid-1-pyrrolidinyl)phenol, 5-chloro-3-(2-carboxamide-1-pyrrolidinyl)phenol, 5-chloro-3-(2-hydroxy-1-pyrrolidinyl)phenol, 5-chloro-3-(2-hydroxymethyl-1-pyrrolidinyl)phenol, 5-chloro-3-(2-methoxymethyl-1-pyrrolidinyl)phenol,
   5-chloro-3-(3-carboxylic acid-1-pyrrolidinyl)phenol,
   5-chloro-3-(3-carboxamide-1-pyrrolidinyl)phenol,
   5-chloro-3-(3-hydroxy-1-pyrrolidinyl)phenol, 5-chloro-3-(3-hydroxymethyl-1-pyrrolidinyl)phenol, 5-chloro-3-(3-methoxymethyl-1-pyrrolidinyl)phenol, 5-fluoro-3-(2-carboxylic acid-1-pyrrolidinyl)phenol, 5-fluoro-3-(2-carboxamide-1-pyrrolidinyl)phenol, 5-fluoro-3-(2-hydroxy-1-pyrrolidinyl)phenol, 5-fluoro-3-(2-hydroxymethyl-1-pyrrolidinyl)phenol, 5-fluoro-3-(2-methoxymethyl-1-pyrrolidinyl)phenol,
   5-fluoro-3-(3-carboxylic acid-1-pyrrolidinyl)phenol,
   5-fluoro-3-(3-carboxamide-1-pyrrolidinyl)phenol,
   5-fluoro-3-(3-hydroxy-1-pyrrolidinyl)phenol, 5-fluoro-3-(3-hydroxymethyl-1-pyrrolidinyl)phenol, 5-fluoro-3-(3-methoxymethyl-1-pyrrol idinyl)phenol, 5-methoxy-3-(2-carboxylic acid-1-pyrrolidinyl)phenol,
   5-methoxy-3-(2-carboxamide-1-pyrrolidinyl)phenol,
   5-methoxy-3-(2-hydroxy-1-pyrrolidinyl)phenol, 5-methoxy-3-(2-hydroxymethyl-1-pyrrolidinyl)phenol, 5-methoxy-3-(2-methoxymethyl-1-pyrrolidinyl)phenol,
   5-methoxy-3-(3-carboxylic acid-1-pyrrolidinyl)phenol,
   5-methoxy-3-(3-carboxamide-1-pyrrolidinyl)phenol,
   5-methoxy-3-(3-hydroxy-1-pyrrolidinyl)phenol, 5-methoxy-3-(3-hydroxymethyl-1-pyrrolidinyl)phenol,
   5-methoxy-3-(3-methoxymethyl-1-pyrrolidinyl)phenol,
   6-chloro-3-(2-carboxylic acid-1-pyrrolidinyl)phenol,
   6-chloro-3-(2-carboxamide-1-pyrrolidinyl)phenol, 6-chloro-3-(2-hydroxy-1-pyrrolidinyl)phenol, 6-chloro-3-(2-hydroxymethyl-1-pyrrolidinyl)phenol, 6-chloro-3-(2-methoxymethyl-1-pyrrolidinyl)phenol, 6-chloro-3-(3-carboxylic acid-1-pyrrolidinyl)phenol, 6-chloro-3-(3-carboxamide-1-pyrrolidinyl)phenol, 6-chloro-3-(3-hydroxy-1-pyrrolidinyl)-phenol, 6-chloro-3-(3-hydroxymethyl-1-pyrrolidinyl)phenol, 6-chloro-3-(3-methoxymethyl-1-pyrrolidinyl)phenol, 6-fluoro-3-(2-carboxylic acid-1-pyrrolidinyl)phenol, 6-fluoro-3-(2-carboxamide-1-pyrrolidinyl)phenol, 6-fluoro-3-(2-hydroxy-1-pyrrolidinyl)phenol, 6-fluoro-3-(2-hydroxymethyl-1-pyrrolidinyl)phenol, 6-fluoro-3-(2-methoxymethyl-1-pyrrolidinyl)phenol, 6-fluoro-3-(3-carboxylic acid-1-pyrrolidinyl)phenol,
   6-fluoro-3-(3-carboxamide-1-pyrrolidinyl)phenol,
   6-fluoro-3-(3-hydroxy-1-pyrrolidinyl)-phenol, 6-fluoro-3-(3-hydroxymethyl-1-pyrrolidinyl)phenol, 6-fluoro-3-(3-methoxymethyl-1-pyrrolidinyl)phenol, 6-methoxy-3-(2-carboxylic acid-1-pyrrolidinyl)phenol, 6-methoxy-3-(2-carboxamide-1-pyrrolidinyl)phenol, 6-methoxy-3-(2-hydroxy-1-pyrrolidinyl)phenol, 6-methoxy-3-(2-hydroxy-methyl-1-pyrrolidinyl)phenol, 6-methoxy-3-(2-methoxymethyl-1-pyrrolidinyl)phenol, 6-methoxy-3-(3-carboxylic acid-1-pyrrolidinyl)phenol, 6-methoxy-3-(3-carboxamide-1-pyrrolidinyl)phenol, 6-methoxy-3-(3-hydroxy-1-pyrrolidinyl)phenol, 6-methoxy-3-(3-hydroxymethyl-1-pyrrolidinyl)phenol, 6-methoxy-3-(3-methoxymethyl-1-pyrrolidinyl)phenol, 2-2-hydroxyethyl-3-(1-pyrrolidinyl)phenol, 2-ethyl-3-(1-pyrrolidinyl)phenol, 2-methyl-3-(1-pyrrolidinyl)phenol, 2-trifluormethyl-3-(1-pyrrolidinyl)phenol, 5-2-hydroxyethyl-3-(1-pyrrolidinyl)phenol, 5-ethyl-3-(1-pyrrolidinyl)phenol, 5-methyl-3-(1-pyrrolidinyl)phenol, 5-trifluormethyl-3-(1-pyrrolidinyl)phenol, 6-2-hydroxyethyl-3-(1-pyrrolidinyl)phenol, 6-ethyl-3-(1-pyrrolidinyl)phenol, 6-methyl-3-(1-pyrrolidinyl)phenol, 6-trifluormethyl-3-(1-pyrrolidinyl)phenol, 2-(2-hydroxyethyl)-3-(2-(2-hydroxyethyl)-1-pyrrolidinyl)phenol, 2-(2-hydroxyethyl)-3-(2-carboxylic acid-1-pyrrolidinyl) phenol, 2-(2-hydroxyethyl)-3-(2-carboxamide-1-pyrrolidinyl)phenol, 2-(2-hydroxy-ethyl)-3-(2-hydroxy -1-pyrrolidinyl) phenol, 2-(2-hydroxyethyl)-3-(2-hydroxy-methyl-1-pyrrolidinyl)phenol, 2-(2-hydroxyethyl)-3-(2-methoxymethyl-1-pyrrolidinyl)phenol, 2-(2-hydroxyethyl)-3-(3-(2-hydroxyethyl)-1-pyrrolidinyl)-phenol, 2-(2-hydroxyethyl)-3-(3-carboxylic acid-1-pyrrolidinyl)phenol, 2-(2-hydroxyethyl)-3-(3-carboxamide-1-pyrrolidinyl)phenol, 2-(2-hydroxy-ethyl)-3-(3-hydroxy -1-pyrrolidinyl) phenol, 2-(2-hydroxyethyl)-3-(3-hydroxy-methyl-1-pyrrolidinyl)phenol, 2-(2-hydroxyethyl)-3-(3-methoxymethyl-1-pyrrolidinyl)phenol, 2-ethyl-3-(2-(2-hydroxyethyl)-1-pyrrolidinyl)phenol, 2-ethyl-3-(2-carboxylic acid-1-pyrrolidinyl)phenol, 2-ethyl-3-(2-carboxamide-1-pyrrolidinyl)phenol, 2-ethyl-3-(2-hydroxy-1-pyrrolidinyl)-phenol, 2-ethyl-3-(2-hydroxymethyl-1-pyrrolidinyl)phenol, 2-ethyl-3-(2-methoxymethyl-1-pyrrolidinyl)phenol, 2-ethyl-3-(3-(2-hydroxyethyl)-1-pyrrolidinyl)phenol, 2-ethyl-3-(3-carboxylic acid-1-pyrrolidinyl)phenol, 2-ethyl-3-(3-carboxamide-1-pyrrolidinyl)phenol, 2-ethyl-3-(3-hydroxy-1-pyrrolidinyl)phenol, 2-ethyl-3-(3-hydroxymethyl-1-pyrrolidinyl)phenol, 2-ethyl-3-(3-methoxymethyl-1-pyrrolidinyl)phenol, 2-methyl-3-(2-(2-hydroxyethyl)-1-pyrrolidinyl)phenol, 2-methyl-3-(2-carboxylic acid-1-pyrrolidinyl)phenol, 2-methyl-3-(2-carboxamide-1-pyrrolidinyl)phenol, 2-methyl-3-(2-hydroxy-1-pyrrolidinyl)phenol, 2-methyl-3-(2-hydroxymethyl-1-pyrrolidinyl)phenol, 2-methyl-3-(2-methoxymethyl-1-pyrrolidinyl)phenol, 2-methyl-3-(3-(2-hydroxyethyl)-1-pyrrolidinyl)phenol, 2-methyl-3-(3-carboxylic acid-1-pyrrolidinyl)phenol, 2-methyl-3-(3-carboxamide-1-pyrrolidinyl)phenol, 2-methyl-3-(3-hydroxy-1-pyrrolidinyl)phenol, 2-methyl-3-(3-hydroxymethyl-1-pyrrolidinyl)phenol, 2-methyl-3-(3-methoxymethyl-1-pyrrolidinyl)phenol, 2-trifluormethyl-3-(2-(2-hydroxyethyl)-1-pyrrolidinyl)-phenol, 2-trifluormethyl-3-(2-carboxylic acid-1-pyrrolidinyl)phenol,
2-trifluormethyl-3-(2-carboxamide-1-pyrrolidinyl)phenol, 2-trifluormethyl-3-(2-hydroxy-1-pyrrolidinyl)phenol, 2-trifluormethyl-3-(2-hydroxymethyl-1-pyrrolidinyl)phenol, 2-trifluormethyl-3-(2-methoxymethyl-1-pyrrolidinyl)-phenol, 2-trifluormethyl-3-(3-(2-hydroxyethyl)-1-pyrrolidinyl)phenol,
2-trifluormethyl-3-(3-carboxylic acid-1-pyrrolidinyl)phenol, 2-trifluormethyl-3-(3-carboxamide -1-pyrrolidinyl)phenol, 2-trifluormethyl-3-(3-hydroxy-1-pyrrolidinyl)phenol, 2-trifluormethyl-3-(3-hydroxymethyl-1-pyrrolidinyl)-phenol, 2-trifluormethyl-3-(3-methoxymethyl-1-pyrrolidinyl)phenol,
5-(2-hydroxyethyl)-3-(2-(2-hydroxyethyl)-1-pyrrolidinyl)phenol,
5-(2-hydroxyethyl)-3-(2-carboxylic acid-1-pyrrolidinyl)phenol, 5-(2-hydroxy-ethyl)-3-(2-carboxamide-1-pyrrolidinyl)phenol, 5-(2-hydroxyethyl)-3-(2-hydroxy-1-pyrrolidinyl)phenol, 5-(2-hydroxyethyl)-3-(2-hydroxymethyl-1-pyrrolidinyl)phenol, 5-(2-hydroxyethyl)-3-(2-methoxymethyl-1-pyrrolidinyl)-phenol, 5-(2-hydroxyethyl)-3-(3-(2-hydroxyethyl)-1-pyrrolidinyl)phenol,
5-(2-hydroxyethyl)-3-(3-carboxylic acid-1-pyrrolidinyl)phenol, 5-(2-hydroxy-ethyl)-3-(3-carboxamide-1-pyrrolidinyl)phenol, 5-(2-hydroxyethyl)-3-(3-hydroxy-1-pyrrolidinyl)phenol, 5-(2-hydroxyethyl)-3-(3-hydroxymethyl-1-pyrrolidinyl)phenol, 5-(2-hydroxyethyl)-3-(3-methoxymethyl-1-pyrrolidinyl)-phenol, 5-ethyl-3-(2-(2-hydroxyethyl)-1-pyrrolidinyl)phenol, 5-ethyl-3-(2-carboxylic acid-1-pyrrolidinyl)phenol, 5-ethyl-3-(2-carboxamide-1-pyrrolidinyl)phenol, 5-ethyl-3-(2-hydroxy-1-pyrrolidinyl)phenol, 5-ethyl-3-(2-hydroxymethyl-1-pyrrolidinyl)phenol, 5-ethyl-3-(2-methoxymethyl-1-pyrrolidinyl)phenol, 5-ethyl-3-(3-(2-hydroxyethyl)-1-pyrrolidinyl)phenol,
5-ethyl-3-(3-carboxylic acid-1-pyrrolidinyl)phenol, 5-ethyl-3-(3-carboxamide-1-pyrrolidinyl)phenol, 5-ethyl-3-(3-hydroxy-1-pyrrolidinyl)-phenol, 5-ethyl-3-(3-hydroxymethyl-1-pyrrolidinyl)phenol, 5-ethyl-3-(3-methoxymethyl-1-pyrrolidinyl)phenol, 5-methyl-3-(2-(2-hydroxyethyl)-1-pyrrolidinyl)phenol, 5-methyl-3-(2-carboxylic acid-1-pyrrolidinyl)phenol,
5-methyl-3-(2-carboxamide-1-pyrrolidinyl)phenol, 5-methyl-3-(2-hydroxy-1-pyrrolidinyl)phenol, 5-methyl-3-(2-hydroxymethyl-1-pyrrolidinyl)phenol,
5-methyl-3-(2-methoxymethyl-1-pyrrolidinyl)phenol, 5-methyl-3-(3-(2-hydroxyethyl)-1-pyrrolidinyl)phenol, 5-methyl-3-(3-carboxylic acid-1-pyrrolidinyl)phenol, 5-methyl-3-(3-carboxamide-1-pyrrolidinyl)phenol,
5-methyl-3-(3-hydroxy-1-pyrrolidinyl)phenol, 5-methyl-3-(3-hydroxymethyl-1-pyrrolidinyl)phenol, 5-methyl-3-(3-methoxymethyl-1-pyrrolidinyl)phenol, 5-trifluormethyl-3-(2-(2-hydroxyethyl)-1-pyrrolidinyl)-phenol,
5-trifluormethyl-3-(2-carboxylic acid-1-pyrrolidinyl)phenol, 5-trifluormethyl-3-(2-carboxamide -1-pyrrolidinyl)phenol, 5-trifluormethyl-3-(2-hydroxy-1-pyrrolidinyl)phenol, 5-trifluormethyl-3-(2-hydroxymethyl-1-pyrrolidinyl)-phenol, 5-trifluormethyl-3-(2-methoxymethyl-1-pyrrolidinyl)-phenol,
5-trifluormethyl-3-(3-(2-hydroxyethyl)-1-pyrrolidinyl)phenol, 5-trifluormethyl-3-(3-carboxylic acid-1-pyrrolidinyl)phenol, 5-trifluormethyl-3-(3-carboxamide-1-pyrrolidinyl)phenol, 5-trifluormethyl-3-(3-hydroxy-1-pyrrolidinyl)phenol, 5-trifluormethyl-3-(3-hydroxymethyl-1-pyrrolidinyl)-phenol, 5-trifluormethyl-3-(3-methoxymethyl-1-pyrrolidinyl)phenol,
6-(2-hydroxyethyl)-3-(2-(2-hydroxyethyl)-1-pyrrolidinyl)phenol,
6-(2-hydroxyethyl)-3-(2-carboxylic acid-1-pyrrolidinyl)phenol, 6-(2-hydroxy-ethyl)-3-(2-carboxamide-1-pyrrolidinyl)phenol, 6-(2-hydroxyethyl)-3-(2-hydroxy-1-pyrrolidinyl)phenol, 6-(2-hydroxyethyl)-3-(2-hydroxymethyl-1-pyrrolidinyl)phenol, 6-(2-hydroxyethyl)-3-(2-methoxymethyl-1-pyrrolidinyl)-phenol, 6-(2-hydroxyethyl)-3-(3-(2-hydroxyethyl)-1-pyrrolidinyl)phenol,
6-(2-hydroxyethyl)-3-(3-carboxylic acid-1-pyrrolidinyl)phenol, 6-(2-hydroxy-ethyl)-3-(3-carboxamide-1-pyrrolidinyl)phenol, 6-(2-hydroxyethyl)-3-(3-hydroxy-1-pyrrolidinyl)phenol, 6-(2-hydroxyethyl)-3-(3-hydroxymethyl-1-pyrrolidinyl)phenol, 6-(2-hydroxyethyl)-3-(3-methoxymethyl-1-pyrrolidinyl)-phenol, 6-ethyl-3-(2-(2-hydroxyethyl)-1-pyrrolidinyl)phenol, 6-ethyl-3-(2-carboxylic acid-1-pyrrolidinyl)phenol, 6-ethyl-3-(2-carboxamide-1-pyrrolidinyl)phenol, 6-ethyl-3-(2-hydroxy-1-pyrrolidinyl)phenol, 6-ethyl-3-(2-hydroxymethyl-1-pyrrolidinyl)phenol, 6-ethyl-3-(2-methoxymethyl-1-pyrrolidinyl)phenol, 6-ethyl-3-(3-(2-hydroxyethyl)-1-pyrrolidinyl)phenol,
6-ethyl-3-(3-carboxylic acid-1-pyrrolidinyl)phenol, 6-ethyl-3-(3-carboxamide-1-pyrrolidinyl)phenol, 6-ethyl-3-(3-hydroxy-1-pyrrolidinyl)-phenol, 6-ethyl-3-(3-hydroxymethyl-1-pyrrolidinyl)phenol, 6-ethyl-3-(3-methoxymethyl-1-pyrrolidinyl)phenol, 6-methyl-3-(2-(2-hydroxyethyl)-1-pyrrolidinyl)phenol, 6-methyl-3-(2-carboxylic acid-1-pyrrolidinyl)phenol,
6-methyl-3-(2-carboxamide-1-pyrrolidinyl)phenol, 6-methyl-3-(2-hydroxy-1-pyrrolidinyl)phenol, 6-methyl-3-(2-hydroxymethyl-1-pyrrolidinyl)phenol,
6-methyl-3-(2-methoxymethyl-1-pyrrolidinyl)phenol, 6-methyl-3-(3-(2-hydroxyethyl)-1-pyrrolidinyl)phenol, 6-methyl-3-(3-carboxylic acid-1-pyrrolidinyl)phenol, 6-methyl-3-(3-carboxamide-1-pyrrolidinyl)phenol,
6-methyl-3-(3-hydroxy-1-pyrrol idinyl)phenol, 6-methyl-3-(3-hydroxymethyl-1-pyrrolidinyl)phenol, 6-methyl-3-(3-methoxymethyl-1-pyrrolidinyl)phenol, 6-trifluormethyl-3-(2-(2-hydroxyethyl)-1-pyrrolidinyl)phenol,
6-trifluormethyl-3-(2-carboxylic acid-1-pyrrolidinyl)phenol, 6-trifluormethyl-3-(2-carboxamide-1-pyrrolidinyl)phenol, 6-trifluormethyl -3-(2-hydroxy-1-pyrrolidinyl)phenol, 6-trifluormethyl-3-(2-hydroxymethyl-1-pyrrolidinyl) -phenol, 6-trifluormethyl-3-(2-methoxymethyl-1-pyrrolidinyl)phenol,
6-trifluormethyl-3-(3-(2-hydroxyethyl)-1-pyrrolidinyl)phenol, 6-trifluormethyl-3-(3-carboxylic acid-1-pyrrolidinyl)phenol, 6-trifluormethyl-3-(3-carboxamide-1-pyrrolidinyl)phenol, 6-trifluormethyl-3-(3-hydroxy-1-pyrrolidinyl)phenol, 6-trifluormethyl-3-(3-hydroxymethyl-1-pyrrolidinyl)-phenol and 6-trifluormethyl-3-(3-methoxymethyl-1-pyrrolidinyl)phenol, or the physiologically tolerated salts thereof.

Preferred are compounds of formula (I) wherein (i) R1 denotes hydrogen and/or (ii) R2 denotes hydrogen.

Particularly well suited meta-aminophenol derivatives of formula (I) in terms of the overall invention are 3-(1-pyrrolidinyl)phenol, 4-fluoro-3-(-1-pyrrolidinyl)phenol, 4-chloro-3-(1-pyrrolidinyl)phenol and 2-methyl-3-(1-pyrrolidinyl)phenol or the physiologically tolerated salts thereof.

The compounds of formula (I) can be used as free bases or in the form of their physiologically tolerated salts with inorganic or organic acids such as, for example, hydrochloric, sulfuric, phosphoric, acetic, propionic, lactic, or citric acid.

The colorants of the invention contain the meta-aminophenol derivative of formula (I) in an amount from about 0.005% to 20% by weight, an amount from about 0.01% to 5.0% by weight and particularly from 0.1% to 2.5% by weight being especially preferred.

Suitable developers are preferably 1,4-diaminobenzene (p-phenylene-diamine), 1,4-diamino-2-methylbenzene (p-toluylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 2-(6-2,5-methyl-pyridin-2-yl)-benzene-1,4-diamine, 2-thiazol-2-yl-benzene-1,4-diamino, 1,4-diamino-2-(pyridin-3-yl)benzene, 2,5-diaminobiphenyl, 2,5-diamino-4'-(1-methylethyl)-1,1'-biphenyl, 2,3',5-triamino-1,1'-biphenyl, 2'-chloro-1,1'-biphenyl-2,5-diamine, 3'-fluoro-1,1'-biphenyl-2,5-diamine, 1,4-diamino-2-methoxymethylbenzene, 1,4-diamino-2-aminomethylbenzene, 3-(3-amino-phenylamino-propenyl)-1,4-diaminobenzene, 1,4-diamino-2-propenylbenzene,1,4-diamino-2-((phenylamino)methyl)-benzene, 1,4-diamino-2-((ethyl-(2-hydroxyethyl)-amino)methyl)benzene, 1,4-diamino-2-hydroxymethylbenzene, 1,4-diamino-2-(2-hydroxyethoxy)-benzene, 2-(2-(acetylamino)ethoxy)-1,4-diaminobenzene, 4-(phenyl-amino)aniline, 4-(dimethylamino)aniline, 4-(diethylamino)aniline, 4-(dipropylamino)aniline, 4-[ethyl(2-hydroxyethyl)amino]aniline, 4-[di(2-hydroxyethyl)amino] aniline, 4-[di (2-hydroxyethyl)amino]-2-methyl-aniline, 4-[(2-methoxyethyl)amino]aniline, 4-[(3-hydroxypropyl) amino]aniline, 4-[(2,3-dihydroxypropyl)amino]aniline, 4-(((4-aminophenyl)methyl)amino)aniline, 4-[(4-amino -phenylamino)-methyl]-phenol, 3-((4-amino-phenylamino) methyl)phenol, 1,4-diamino-N-(4-pyrrolidin-1-yl-benzyl) benzene, 1,4-diamino-N-furan-3-ylmethylbenzene, 1,4-diamino-N -thiophen-2-ylmethylbenzene, 1,4-diamino-N-furan-2-ylmethylbenzene, 1,4-diamino-N-thiophen-3-ylmethylbenzene, 1,4-diamino-N-benzylbenzene, 1,4-diamino-2-(1-hydroxyethyl)benzene, 1,4-diamino-2-(2-hydroxyethyl)-benzene, 1,4-diamino-2-(1-methylethyl) -benzene, 1,3-bis[(4-aminophenyl)-(2-hydroxyethyl) amino]-2-propanol, 1,4-bis[(4-aminophenyl) -amino]-butane, 1,8-bis(2,5-diaminophenoxy)-3,6-dioxaoctane, 2,5-diamino-4'-hydroxy-1,1'-biphenyl, 2,5-diamino-2'-trifluormethyl-1,1'-biphenyl, 2,4',5-triamino-1,1'-biphenyl, 4-amino-phenol, 4-amino-3-methylphenol, 4-amino-3-(hydroxymethyl) -phenol, 4-amino-3-fluoro-phenol, 4-methylamino-phenol, 4-amino-2-(aminomethyl)phenol, 4-amino-2-(hydroxymethyl)phenol, 4-amino-2-fluorophenol, 4-amino-2-[(2-hydroxyethyl)-amino]methyl-phenol, 4-amino-2-methyl -phenol, 4-amino-2-(methoxymethyl) phenol, 4-amino-2-(2-hydroxyethyl)phenol, bis(5-amino-2-hydroxyphenyl)phenol, 5-amino-salicylic acid, 2,5-diamino-pyridine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl) methyl]-4,5-diamino-1H-pyrazole, 4,5-diamino-1-methyl-1H-pyrazole, 4,5-diamino-1-pentyl-1H-pyrazole, 4,5-diamino-1-(phenylmethyl)-1H-pyrazole, 4,5-diamino-1-((4-methoxyphenyl)methyl-1H-pyrazole, 2-aminophenol, 2-amino-6-methylphenol, 2-amino-5-methyl-phenol, 4-amino-1,1'-biphenyl-3-ol, 2-amino-5-ethylphenol, 1,2,4-trihydroxybenzene, 2,4-diaminophenol, 1,4-dihydroxybenzene and 2-(((4-aminophenyl)amino)methyl)-1,4-diaminobenzene.

Furthermore, in addition to the compounds of the formula (I), the colorant according to the invention can also comprise further known coupler substances, for example N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino -1-ethoxy-5-methylbenzene, 2,4-diamino-1-(2-hydroxyethoxy)-5-methylbenzene, 2,4-di[(2-hydroxyethyl) amino]-1,5-dimethoxybenzene, 2,3-diamino-6-methoxypyridine, 3-amino-6-methoxy-2-(methylamino)-pyridine, 2,6-diamino -3,5-dimethoxypyridine, 3,5-diamino-2,6-dimethoxy-pyridine, 1,3-diaminobenzene, 2,4-diamino -1-(2-hydroxyethoxy)benzene, 1,3-diamino-4-(2,3-dihydroxypropoxy)benzene, 1,3-diamino-4-(3-hydroxypropoxy)benzene, 1,3-diamino-4-(2-methoxyethoxy) benzene, 2,4-diamino-1,5-di(2-hydroxyethoxy)benzene, 1-(2-aminoethoxy)-2,4-diaminobenzene, 2-amino-1-(2-hydroxyethoxy) -4-methylaminobenzene, 2,4-diamino-phenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl) amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)-amino]acetamide, 5-[(2-hydroxyethyl) amino]-4-methoxy-2-methylphenol, 5-[(2-hydroxyethyl) amino]-2-methylphenol, 3-[(2-hydroxyethyl)amino]-phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)-amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxy-naphthalene, 1,7-dihydroxy -naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1, 3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4 (2H)-benzoxazine, 6-amino-3,4-dihydro-1,4(2H)-benzoxazine, 3-methyl-1-phenyl-5-pyrazolone, 5,6-dihydroxyindole, 5,6-dihydroxy-indoline, 5-hydroxyindole, 6-hydroxyindole, 7-hydroxyindole and 2,3-indolinedione.

The additional coupler substances and developer substances may be present in the colorant according to the invention in each case individually or in the mixture with one another, where the total amount of coupler substances and developer substances in the colorant according to the invention (based on the total amount of the colorant) is in each case about 0.005% to 20% by weight, preferably about 0.01% to 5% by weight and in particular 0.1% to 2.5% by weight.

The total amount of the developer substance-coupler substance combination present in the colorant according to the invention is preferably about 0.01% to 20% by weight, particularly preferred is an amount of from about 0.02% to 10% by weight and especially 0.2% to 6% by weight. The developer substances and coupler substances are generally used in approximately equimolar amounts; however, it is not disadvantageous if the developer substances are present in this regard in a certain excess or deficit, for example a coupler: developer ratio of from 1:2 to 1:0.5.

In addition, the colorant according to the invention can additionally comprise other color components, for example 6-amino-2-methylphenol and 2-amino-5-methylphenol, and also customary natural, nature-identical or synthetic direct dyes, for example triphenylmethane dyes, such as
4-[(4'-aminophenyl)(4'imino-2",5"-cyclohexadien-1"-ylidene)methyl]-2-methylaminobenzene monohydrochloride (C.I. 42 510) and 4-[(4'-amino-3'-methylphenyl)(4"-imino-3"-methyl-2",5"-cyclohexadien-1"-ylidene)-methyl]-2-methylaminobenzene monohydrochloride (C.I. 42 520), aromatic nitro dyes, such as 4-(2'-hydroxyethyl)aminonitrotoluene, 2-amino-4,6-dinitrophenol,
2-amino-5-(2'-hydroxyethyl)aminonitrobenzene, 2-chloro-6-(ethylamino)-4-nitrophenol,
4-chloro-N-(2-hydroxyethyl-2-nitroaniline,
5-chloro-2-hydroxy-4-nitroaniline, 2-amino-4-chloro-6-nitrophenol or
1-[(2'-ureidoethyl)amino-4-nitrobenzene, azo dyes, such as
6-[(4'-aminophenyl)azo]-5-hydroxynaphthalene-1-sulfonic acid sodium salt (C.I. 14 805) or dispersion dyes, such as, for example, 1,4-diamino-anthraquinone and 1,4,5,8-tetraaminoanthraquinone, and basic or acidic direct dyes. The colorant can comprise these color components in an amount of from about 0.1% to 4.0% by weight.

The coupler substances and developer substances and also the other color components, if they are bases, can of course also be used in the form of the physiologically compatible salts with organic or inorganic acids, such as, for example, hydrochloric acid, sulfuric acid, or phosphoric acid, or—if they have aromatic OH groups—in the form of these salts with bases, for example as alkali metal phenoxides.

Moreover, if the colorants are to be used for dyeing hair, they may also comprise further customary cosmetic additives, for example antioxidants, such as ascorbic acid, thioglycolic acid, and sodium sulfite, and perfume oils, complexing agents, wetting agents, emulsifiers, thickeners, and care substances. The preparation form of the colorant according to the invention can, for example, be a solution, in particular an aqueous or aqueous-alcoholic solution. The particularly preferred preparation forms are, however, a cream, a gel, or an emulsion. Their composition is a mixture of the dye components with the additives customary for such preparations.

Customary additives in solutions, creams, emulsions, or gels are, for example, solvents, such as water, lower aliphatic alcohols, for example ethanol, propanol or isopropanol, glycerol or glycols, such as 1,2-propylene glycol, and also wetting agents or emulsifiers from the classes of anionic, cationic, amphoteric or nonionogenic surface-active substances, such as, for example, fatty alcohol sulfates, oxyethylated fatty alcohol sulfates, alkylsulfonates, alkylbenzenesulfonates, alkyltrimethylammonium salts, alkylbetaines, oxyethylated fatty alcohols, oxyethylated nonylphenols, fatty acid alkanolamides, and oxyethylated fatty acid esters, also thickeners, such as higher fatty alcohols, starch, cellulose derivatives, petrolatum, paraffin oil, and fatty acids, and also care substances, such as cationic resins, lanolin derivatives, cholesterol, pantothenic acid, and betaine. The constituents mentioned are used in the amounts customary for such purposes, for example the wetting agents and emulsifiers in concentrations of from about 0.5% to 30% by weight, the thickeners in an amount of from about 0.1% to 25% by weight, and the care substances in a concentration of from about 0.1% to 5% by weight.

Depending on the composition, the colorant of the invention can be weakly acidic, neutral, or alkaline. In particular, it has a pH from 6.8 to 11.5.

According to the present invention for pH adjustment in the alkaline range the composition may further optionally comprise at least one source of alkalizing agent, preferably a source of ammonium ions and or ammonia. Any agent known in the art may be used such as alkanolamides for example monoethanolamine, diethanolamine, triethanolamine, monopropanolamine, dipropanolamine, tripropanolamine, 2-amino-2-methyl-1, 3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia, and mixtures thereof. Particularly preferred are ammonium carbonate, ammonium carbamate, ammonium hydrogen carbonate, ammonia, and mixtures thereof, or a mixture of ammonia and organic amines (particularly monoethanolamine or triethanolamine). The compositions of the present invention may comprise from about 0.1% to about 10% by weight, preferably from about 0.5% to about 5%, most preferably from about 1% to about 3% of an alkalizing agent, preferably ammonium ions.

For pH adjustment in the acidic range, an inorganic or organic acid, for example phosphoric acid, acetic acid, citric acid, or tartaric acid, may be used.

The compositions according to the present invention may comprise at least one source of an oxidizing agent for developing the hair color. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilization and decolourization of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates, and the like. These inorganic perhydrate salts may be incorporated as monohydrates, tetrahydrates etc. Alkyl and aryl peroxides, and/or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates, and combinations thereof.

According to the present invention the compositions comprise from about 0.1% to about 15% by weight, preferably from about 1% to about 10% by weight, and most preferably from about 2% to about 7% by weight of an oxidizing agent.

Another preferred oxidizing agent for use herein is a source of peroxymonocarbonate ions. Preferably such a source is formed insitu from a source of hydrogen peroxide and a hydrogen carbonate ion source. Such an oxidizing agent has been found to be particularly effective at a pH of up to and including 9.5, preferably 7.5 to 9.5 more preferably about pH 9. Moreover, this system is also particularly effective in combination with a source of ammonia or ammonium ions. It has been found that this oxidizing agent can deliver improvements to the desired hair colour results particularly with regard to the delivery of high lift, while considerably reducing the odour, skin and scalp irritation and damage to the hair fibers.

Accordingly, any source of these ions may be utilized. Suitable sources for use herein include sodium, potassium, guanidine, arginine, lithium, calcium, magnesium, barium, ammonium salts of carbonate, carbamate and hydrocarbonate ions, and mixtures thereof, such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate, and mixtures thereof. Percarbonate salts may also be utilized to provide both the source of carbonate ions and oxidizing agent. Preferred sources of carbonate ions, carbamate, and hydrocarbonate ions are sodium hydrogen carbonate, potassium hydrogen carbonate, ammonium carbamate, and mixtures thereof.

According to the present invention the compositions comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of a source of hydrogen peroxide.

Especially preferred oxidants for developing the hair color are mainly hydrogen peroxide or a compound of addition of hydrogen peroxide to urea, melamine, sodium borate, or sodium carbonate, in the form of a 3 to 12%, preferably 6%, aqueous solution, as well as air oxygen. When a 6% hydrogen peroxide solution is used as the oxidant, the weight ratio of hair colorant to oxidant is 5:1 to 2:1, and preferably 1:1. Larger amounts of oxidant are used primarily when the hair colorant contains a higher dye concentration or when stronger hair bleaching is desired at the same time.

According to the present invention the compositions may further comprise a source of radical scavenger. As used herein the term radical scavenger refers to a species that can react with a reactive radical, preferably carbonate radicals, to convert the reactive radical by a series of fast reactions to a less reactive species. Suitable radical scavengers for use herein include compounds according to the general formula (II):

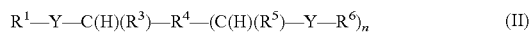

$$R^1-Y-C(H)(R^3)-R^4-(C(H)(R^5)-Y-R^6)_n \quad (II)$$

wherein Y is $NR^2$, O, or S, preferably $NR^2$, n is 0 to 2, and wherein $R^4$ is monovalent or divalent and is selected from: (a) substituted or unsubstituted, straight or branched, alkyl, mono- or poly-unsaturated alkyl, heteroalkyl, aliphatic, heteroaliphatic, or heteroolefinic systems; (b) substituted or unsubstituted, mono- or poly-cyclic aliphatic, aryl, or heterocyclic systems; or (c) substituted or unsubstituted, mono-, poly-, or per-fluoro alkyl systems; the systems of (a), (b), and (c) comprising from 1 to 12 carbon atoms and 0 to 5 heteroatoms selected from O, S, N, P, and Si; and wherein $R^4$ can be connected to $R^3$ or $R^5$ to create a 5, 6 or 7 membered ring; and wherein $R^1$, $R^2$, $R^3$, $R^5$, and $R^6$ are monovalent and are selected independently from: (a), (b), and (c) described herein above, or H.

Preferably, $R^4$ is selected from: (a) substituted or unsubstituted, straight or branched, alkyl, heteroalkyl, aliphatic, heteroaliphatic, or heteroolefinic systems; (b) substituted or unsubstituted, mono- or poly-cyclic aliphatic, aryl, or heterocyclic systems; or (c) substituted or unsubstituted, mono-, poly-, or per-fluoro alkyl systems; more preferably $R^4$ is selected from (a) substituted or unsubstituted, straight or branched, alkyl, heteroalkyl, aliphatic, or heteroaliphatic systems; (b) substituted or unsubstituted, aryl, or heterocyclic systems; or (c) substituted or unsubstituted, mono-, poly-, or per-fluoro alkyl systems; more preferably substituted or unsubstituted, straight or branched, alkyl, or heteroalkyl systems.

Preferably, the $R^4$ systems of (a), (b), and (c), described herein above, comprise from 1 to 8 carbon atoms, preferably from 1 to 6, more preferably from 1 to 4 carbon atoms and from 0 to 3 heteroatoms; preferably from 0 to 2 heteroatoms; most preferably from 0 to 1 heteroatoms. Where the systems contain heteroatoms, preferably they contain 1 eteroatom. Preferred heteroatoms include O, S, and N; more preferred are O and N; O being paricularly preferred.

Preferably, $R^1$, $R^2$, R, $R^5$, and $R^6$ are selected independently from any of the systems defined for $R^4$ above, and H.

In alternative embodiments, any of $R^1$, $R^2$, $R^3$, $R^4$, $R^5$, and $R^6$ groups are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems; (ii) substituted or unsubstituted, mono- or poly-cyclic aliphatic, aryl, or heterocyclic system; or (iii) substituted or unsubstituted, monofluoroalkyl, polyfluoroalkyl or perfluoroalkyl systems; said systems of (i), (ii), and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, $N=NA^1$, $N=NOA^1$, $NA^1CN$, $NA^1NA^2A^3$; (e) the group of monovalent substituents consisting of $COOA^1$, $CON_3$, $CONA^1_2$, $CONA^1COA^2$, $C(=NA^1)NA^1A^2$, CHO, CHS, CN, NC, and X; and (f) the group consisting fluoroalkyl monovalent substituents consisting of monofluoroalkyl, polyfluoroalkyl perfluoroalkyl systems comprising from 1 to 12 carbon atoms and 0 to 4 heteroatoms.

For the groups (b) to (e), described above, $A^1$, $A^2$, and $A^3$ are monovalent and are independently selected from: (1) H; (2) substituted or unsubstituted, straight or branched, alkyl, monounsaturated or poly-unsaturated alkyl, heteroalkyl, aliphatic, heteroaliphatic or heteroolefinic systems; (3) substituted or unsubstituted, monocyclic or polycyclic aliphatic, aryl or heterocyclic systems; or (4) substituted or unsubstituted, monofluoroalkyl, polyfluoroalkyl or perfluoroalkyl systems; said systems of (2), (3), and (4) comprising from 1 to 10 carbon atoms and 0 to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in *Advanced Organic Chemistry—Reactions, Mechanisms and Structure* (Jerry March, 5$^{th}$ ed. (2001) at pages 368-375).

Alternative suitable radical scavengers for use herein are compounds according to the general formula (III):

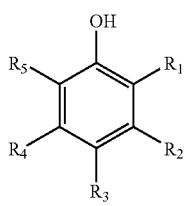

wherein $R_1$, $R_2$, $R_3$, $R_4$, and $R_5$ are each independently selected from H, $COO^-M^+$, Cl, Br, $SO_3^-M^+$, $NO_2$, $OCH_3$, OH, or a $C^1$ to $C^{10}$ primary or secondary alkyl and M is either H or alkali metal. Preferably, the above-described radical scavengers have a pKa of more than 8.5 to ensure protonation of the hydroxy goup.

Other suitable radical scavengers for use herein include those selected from group (III) benzylamine, imidazole, di-tert-butylhydroxytoluene, hydroquinone, guanine, pyrazine, piperidine, morpholine, methylmorpholine, 2-methyoxy-ethylamine, and mixtures thereof.

Preferred radical scavengers according to the present invention are selected from the classes of alkanolamines, amino sugars, amino acids, esters of amino acids, and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof, and mixtures thereof. Especially preferred compounds are glycine, sarcosine, lysine, serine, 2 methoxyethylamine, glucosamine, glutamic acid, morpholine, piperdine, ethylamine, 3 amino-1-propanol, and mixtures thereof.

The radical scavengers according to the present invention preferably have a molecular weight of less than about 500, preferably less than about 300, more preferably less than about 250 in order to facilitate penetration of the radical scavenger into the hair fiber. The compositions of the present invention preferably comprise from about 0.1% to about 10% by weight, preferably from about 1% to about 7% by weight of radical scavenger. The radical scavenger is also preferably selected such that it is not an identical species as the alkalizing agent. According to one embodiment of the present invention the radical scavenger may be formed insitu in the hair dyeing compositions prior to application to the hair fibers.

To use the afore-described colorants for oxidative dyeing of hair, said colorants are mixed with an oxidant immediately before use, and the mixture is applied to hair in an amount sufficient for hair treatment which, depending on hair fullness, is generally from about 60 to 200 grams.

Suitable oxidants for developing the hair color are mainly hydrogen peroxide or a compound resulting from the addition of hydrogen peroxide to urea, melamine, sodium borate, or sodium carbonate, in the form of a 3 to 12% by weight, preferably 6% by weight, aqueous solution, as well as air oxygen. When a 6% hydrogen peroxide solution is used as the oxidant, the weight ratio of hair colorant to oxidant is 5:1 to 2:1, and preferably 1:1. Larger amounts of oxidant are used primarily when the hair colorant contains a higher dye concentration or when stronger hair bleaching is desired at the same time.

The mixture is allowed to act on the hair at 15 to 50° C. for about 10 to 45 minutes and preferably for 30 minutes. The hair is then rinsed with water and dried. Optionally, this rinse can be followed with a shampoo wash, optionally followed by rinsing with a weak organic acid, for example citric or tartaric acid. The hair is then dried.

The hair dyes according to the invention with a content of m-aminophenol derivatives of formula (I) as coupler substances permit hair colorations with excellent color fastness, in particular with regard to washing fastness and rubbing fastness. With regard to the coloring properties, the hair colorants according to the invention offer, depending on the nature and composition of the color components, a broad palette of different shades which ranges from brown, purple, violet to blue, and black shades. The color intensity of the color shades is particularly good. The very good coloring properties of the hair colorants according to the present application are further evident from the fact that these agents permit a coloring of gray, chemically non-predamaged hair without problems and with good coverage.

The following examples illustrate the object of the invention in more detail without limiting ist scope.

EXAMPLES

Example 1

Synthesis of 3-(1-pyrrolidinyl)phenol

A. Synthesis of 1-Bromo-3-methoxymethoxy-benzene

To a solution of 31.4 g (183.3 mmol) of 3-Bromo-phenol in 450 mL of dried acetonitrile a dispersion of 12 g (274.9 mmol) of sodium hydride (55% in oil) was added portionwise at 0° C. The mixture was then allowed to agitate at 0° C. for 3 hours. A solution of 25 g (210.8 mmol) of chloromethyl ethyl ether in 30 mL of acetonitrile was added dropwise, and the mixture was allowed to agitate overnight at room temperature (20-30° C.). The reaction mixture was then filtered and the filter cake was washed with a small amount of acetone. The combined filtrates were evaporated. This gave 32.3 g of 1-Bromo-3-methoxymethoxy-benzene. The resulting crude product was used in the next step without further purification.

$^1$H-NMR (300 MHz, DMSO): 7.26-7.16 ppm (m 3H); 7.02 ppm (dd, 1H); 5.25 ppm (s, 2H); 3.65 ppm (q, 2H); 3.5 ppm (t, 3H).

B. Synthesis of 3-(1-pyrrolidinyl)phenol 7 g (30 mmol) of 1-Bromo-3-methoxymethoxy-benzene from step A and 2.5 g (35 mmol) of pyrrolidine were dissolved under argon in 60 mL of toluene. Then, 0.15 g (0.3 mmol) of bis(tri-t-butylphosphine)palladium(0), 2.5 g KOH und 0.6 g (0.15 mmol) cetyltrimethylammoniumbromid were added, and the reaction mixture was heated at 80° C. At the end of the reaction, the reaction mixture was poured into 200 mL of ethyl acetate, and the organic phase was extracted with 1N sodium hydroxide solution and then dried with magnesium sulfate. The solvent was distilled off in a rotary evaporator, and the residue was purified on silica gel using heptane/ethyl acetate (8/0.8). The product thus obtained was dissolved in 15 mL of ethanol and mixed with 10 mL of a 2.9 molar solution of ethanolic hydrochloric acid. The reaction mixture was then heated at 55° C. At the end of the reaction, the precipitate was filtered off, washed with ethanol, and then dried.

$^1$H-NMR (300 MHz, DMSO): 7.4-6.9 ppm (m 2H); 6.6-6.4 ppm (m, 2H); 3.55-3.4 ppm (m, 4H); 2.15-1.95 ppm (m, 4H).

Examples 2 to 5

Hair Colorants

| | |
|---|---|
| 0.00125 mole | developer according to Table 1 |
| 0.00125 mole | coupler of formula (I) according to Table 1 |
| 10.0 g | potassium oleate (8% aqueous solution) |
| 10.0 g | ammonia (22% aqueous solution) |
| 10.0 g | isopropanol |
| 0.3 g | ascorbic acid |
| to 100.0 g | water |

Immediately before use, 30 g of the above dye solution was mixed with 30 g of a 6% aqueous hydrogen peroxide solution. The mixture was then applied to bleached hair. After an exposure time of 30 minutes at 40° C., the hair was rinsed with water, washed with a commercial shampoo, and dried. The resulting color shades are shown in Table 1.

TABLE 1

| Example | Developer | Coupler of Formula (I) | Color |
|---|---|---|---|
| 2 | 1,4-diamino-benzene | 3-(1-pyrroldinyl)phenol | natural blond |
| 3 | 1,4-diamino-2-methyl-benzene | 3-(1-pyrroldinyl)phenol | natural blond |
| 4 | 1,4-diamino-2-(2-hydroxyethyl)benzene sulfate | 3-(1-pyrroldinyl)phenol | natural blond |
| 5 | 4,5-diamino-1-(2-hydroxyethyl)-1H-pyrazole sulfate | 3-(1-pyrroldinyl)phenol | purple |

Examples 6 to 25

Hair Colorants

| | |
|---|---|
| X g | coupler S1 of formula (I) according to Table 2 |
| U g | primary intermediates E1 to E8 according to Table 3 |
| Y g | coupler K1 to K21 according to Table 2 |
| Z g | direct dye D1 to D3 according to Table 4 |
| 10.0 g | of potassium oleate (8% aqueous solution) |
| 10.0 g | of ammonia (22% aqueous solution) |
| 10.0 g | ethanol |
| 0.3 g | ascorbic acid |
| balance to 100.0 g | water |

Immediately before use, 30 g of the foregoing dye solution was mixed with 30 g of a 6% aqueous hydrogen peroxide solution. The mixture was then applied to bleached hair. After an exposure time of 30 minutes at 40° C., the hair was rinsed with water, washed with a commercial shampoo, and dried. The dye quantity used and the color results are presented in Table 5.

TABLE 2

| | Coupler Substances |
|---|---|
| S1 | 3-(1-pyrrolidinyl)phenol |
| K1 | 1,3-diaminobenzene |
| K2 | 2-amino-4-(2'-hydroxyethyl)amino-anisol-sulfate |
| K3 | 2,4-diamino-1-(2'-hydroxyethoxy)benzene-sulfate |
| K4 | 2,4-diamino-5-fluoro-toluene-sulfate |
| K5 | 3-amino-2-methylamino-6-methoxy-pyridin |
| K6 | 3,5-diamino-2,6-dimethoxy-pyridin-dihydrochloride |
| K7 | 2,4-diamino-5-ethoxy-toluene-sulfate |
| K8 | N-((3-Dimethylamino)phenyl)urea |
| K9 | 1,3-Bis(2,4-diaminophenoxy)propane-tetrahydrochloride |
| K10 | 3-amino-phenol |
| K11 | 5-amino-2-methyl-phenol |
| K12 | 5-amino-6-chlor-2-methyl-phenol |
| K13 | 5-amino-4-fluor-2-methyl-phenol-sulfate |
| K14 | 1-naphthol |
| K15 | 1-acetoxy-2methyl-naphthalene |
| K16 | resorcinol |
| K17 | 2-methyl-resorcinol |
| K18 | 4-chloro-resorcinol |
| K19 | 4-(2'-hydroxyethyl)amino-1,2-methylendioxybenzene*HCl |
| K20 | 3,4-methylendioxy-phenol |
| K21 | 2-amino-5-methyl-phenol |

TABLE 3

| | Developer Substances |
|---|---|
| E1 | 1,4-diamino-2-methyl-benzene sulfate |
| E2 | 1,4-diaminobenzol |
| E3 | 1,4-diamino-2-(2-hydroxyethyl)benzene sulfate |
| E4 | 3-methyl-4-amino-phenol |
| E5 | 4-amino-2-aminomethyl-phenol-dihydrochloride |
| E6 | 4-amino-phenol |
| E7 | N,N-bis(2'-hydroxyethyl)-p-phenylendiamin-sulfate |
| E8 | 4,5-diamino-1-(2-hydroxyethyl)-1H-pyrazole sulfate |

TABLE 4

| | Direct Dyes |
|---|---|
| D1 | 2,6-diamino-3-((pyridin-3-yl)azo)pyridin |
| D2 | 6-chlor-2-ethylamino-4-nitro-phenol |
| D3 | 2-amino-6-chloro-4-nitro-phenol |

TABLE 5

| | Hair Colorants | | | | | |
|---|---|---|---|---|---|---|
| | Example Nr. | | | | | |
| | 6 | 7 | 8 | 9 | 10 | 11 |
| Dye | (Dye quantity in gram) | | | | | |
| S1 | 1.40 | 0.080 | 0.010 | 0.32 | 3.00 | 0.075 |
| E1 | 2.40 | 0.150 | 0.060 | 0.60 | 0.45 | 0.130 |
| K2 | 0.15 | | 0.004 | | 2.00 | 0.015 |
| K10 | 0.30 | 0.005 | | | 0.70 | 0.020 |
| K11 | | | 0.030 | 0.02 | | |
| K14 | | | | | | 0.030 |

TABLE 5-continued

Hair Colorants

| | | | | | | |
|---|---|---|---|---|---|---|
| K17 | | 0.040 | | 0.15 | | |
| D3 | 0.05 | | | 0.01 | | |
| | warm brown | light blond | light aubergine | warm-brown | blue-black | pearlsilver-blond |

| Dye | Example Nr. 12 | 13 | 14 | 15 | 16 | 17 |
|---|---|---|---|---|---|---|
| | (Dye quantity in gram) | | | | | |
| S1 | 1.6 | 0.4 | 1.3 | 0.270 | 0.10 | 0.40 |
| E1 | 1.8 | 0.9 | 2.4 | 0.60 | 0.21 | 0.9 |
| E4 | 0.5 | 0.04 | 0.01 | 0.165 | 0.01 | 0.01 |
| K2 | | | | 0.1 | | |
| K6 | | | 0.070 | | | |
| K8 | 0.03 | | | | | |
| K10 | 0.06 | | 0.42 | 0.8 | | 0.02 |
| K11 | 0.60 | 0.06 | | 0.165 | 0.01 | 0.02 |
| K17 | | 0.32 | | | 0.05 | 0.250 |
| K19 | | | | | | 0.05 |
| K20 | | | | | 0.03 | |
| K21 | | 0.01 | | 0.30 | | |
| D1 | | 0.01 | | | | |
| D2 | | | | 0.01 | | 0.02 |
| D3 | 0.2 | | | | 0.02 | |
| | dark-mahagony | purpur-brown | black-brown | chocolat-brown | blond | brown |

| Dye | Example Nr. 19 | 20 | 21 | 22 | 23 | 24 | 25 |
|---|---|---|---|---|---|---|---|
| | (Dye quantity in gram) | | | | | | |
| S1 | 0.15 | 0.20 | 2.2 | 1.6 | 1.4 | 0.270 | 0.20 |
| E1 | 0.9 | 3.8 | 3.2 | 2.5 | 2.3 | 1.9 | 0.9 |
| E4 | 0.25 | 0.1 | 0.03 | 0.55 | 0.015 | 0.15 | 0.01 |
| K1 | 0.30 | | | | | | |
| K3 | | | 0.25 | | | 0.075 | |
| K4 | | | 0.2 | | | | |
| K5 | | 0.02 | | | 0.065 | | |
| K7 | | | | 0.025 | | | |
| K9 | | 0.15 | | | | | |
| K10 | | | 0.4 | 0.1 | 0.42 | 0.75 | 0.015 |
| K12 | | 0.15 | | 0.6 | | 0.15 | |
| K13 | | | | | | | 0.015 |
| K16 | 0.05 | 0.05 | 1.1 | 0.8 | 0.7 | 0.135 | |
| K17 | | 0.05 | | | | | 0.25 |
| K18 | | 0.60 | | | | | |
| K19 | 1.00 | 1.00 | | | | | 0.05 |
| K21 | 0.20 | | | | | 0.20 | |
| D2 | | | | | | 0.010 | 0.015 |
| D3 | | | | 0.2 | | | |
| | matt | medium-brown | dark-brown | dark-mahagony | black-brown | chocolat-brown | colorado-brown |

Examples 26 to 40

Hair Colorants

| | |
|---|---|
| X g | coupler S1 of formula (I) according to Table 2 |
| U g | primary intermediates E1 to E8 according to Table 3 |
| Y g | coupler K1 to K21 according to Table 2 |
| Z g | direct dye D1 to D3 according to Table 4 |
| 15.0 g | cetylstearyl alcohol |
| 0.3 g | ascorbic acid |
| 3.5 g | sodium lauryl alcohol diglycol ether sulphate (28% aqueous solution) |

-continued

| | |
|---|---|
| 3.0 g | ammonia, 25% aqueous solution |
| 0.3 g | sodium sulphite |
| balance to 100.0 g | water |

Immediately before use, 30 g of the above dye solution was mixed with 30 g of 6% aqueous hydrogen peroxide solution. The mixture was then applied to bleached hair. After an exposure time of 30 minutes at 40° C., the hair was rinsed with water, washed with a commercial shampoo, and dried. The hair had a blond shade. The dye quantity used and the color results are presented in Table 6.

TABLE 6

| Dyes | Example Nr. 26 | 27 | 28 | 29 | 30 | 31 | 32 |
|---|---|---|---|---|---|---|---|
| | (Dye quantity in gram) | | | | | | |
| S1 | 1.7 | 0.5 | 1.30 | 0.30 | 1.70 | 0.50 | 1.30 |
| E1 | 1.45 | 0.70 | 1.70 | 0.55 | | | |
| E2 | | | | | 0.75 | 0.35 | 0.80 |
| E6 | 0.5 | 0.03 | 0.008 | 0.145 | 0.5 | 0.03 | 0.008 |
| K2 | | | | 0.07 | | | |
| K6 | | | 0.07 | | | | 0.07 |
| K8 | 0.03 | | | | 0.03 | | |
| K10 | 0.07 | | 0.415 | 0.80 | 0.07 | | 0.415 |
| K11 | 0.60 | 0.05 | | 0.165 | 0.60 | 0.05 | |
| K16 | | 0.15 | | | | 0.15 | |
| K17 | | 0.10 | | | | 0.05 | |
| K21 | | 0.015 | | 0.275 | | 0.015 | |
| D1 | | 0.010 | | | | 0.010 | |
| D2 | | | | 0.015 | | | |
| D3 | 0.15 | | | | 0.15 | | |
| | dark-mahagony | purpur-brown | black-brown | chocolat-brown | dark-mahagony | purpur-brown | black-brown |

| Dye | Example Nr. 33 | 34 | 35 | 36 | 37 | 38 | 39 | 40 |
|---|---|---|---|---|---|---|---|---|
| | (Dye quantity in gram) | | | | | | | |
| S1 | 2.20 | 0.05 | 0.030 | 0.05 | 2.20 | 0.05 | 0.030 | 0.05 |
| E1 | 2.80 | 0.50 | 0.02 | 1.90 | | | | |
| E2 | | | | | 1.40 | 0.25 | 0.01 | 0.85 |
| E3 | 1.45 | 0.60 | 0.02 | 0.05 | 1.45 | 0.60 | 0.020 | 0.05 |
| E4 | 0.01 | 0.01 | 0.10 | 0.01 | | | | |
| E5 | | | | | 0.015 | 0.015 | 0.15 | 0.015 |
| K1 | 0.20 | | | | 0.20 | | | |
| K2 | 0.60 | | | | 0.60 | | | |
| K3 | | | | 0.30 | | | | 0.30 |
| K5 | | | | 0.05 | | | | 0.05 |
| K6 | 0.01 | | | | 0.01 | | | |
| K7 | | 0.01 | | | | 0.01 | | |
| K8 | | | | 0.50 | | | | 0.5 |
| K9 | 0.08 | | | | 0.80 | | | |
| K10 | 0.30 | 0.03 | 0.02 | | 0.30 | 0.03 | 0.025 | |
| K11 | | | 0.015 | | | | 0.016 | |
| K12 | | | | 0.300 | | | | 0.315 |
| K17 | | 0.05 | 0.10 | 0.20 | | 0.050 | 0.085 | 0.20 |
| K18 | | 0.05 | | | | 0.05 | | |
| K19 | | | 0.01 | | | | 0.01 | |
| K20 | | 0.50 | | | | 0.50 | | |
| K21 | | 0.05 | | | | 0.05 | | |
| | black | brown | light blond | dark-brown | black | brown | light blond | dark-brown |

Unless stated otherwise, all of the percentages given in the present application are percentages by weight.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An agent for the oxidative dyeing of keratin fibers based on a developer substance/coupler substance combination, comprising at least one m-aminophenol derivative of general formula (I), or its physiologically compatible, water-soluble salt,

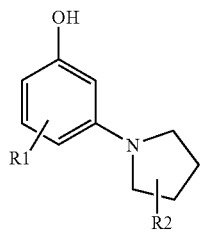

wherein
R1 is selected from the group consisting of hydrogen, a C1-C6 alkyl group, C2-C4 hydroxyalkyl group, a C3-C4 dihydroxyalkyl group, a C1-C4 alkoxy group or a halogen atom; and
R2 is selected from the group consisting of a hydroxy group, a carboxylic group, an aminocarbonylgroup or a hydroxymethyl group.

2. An agent according to claim 1, wherein R1 is hydrogen.

3. An agent according to claim 1, wherein the meta-aminophenol derivative of formula (I) is selected from the group consisting of:
2-chloro-3-(2-carboxylic acid-1-pyrrolidinyl)phenol,
2-chloro-3-(2-carboxamide-1-pyrrolidinyl)phenol,
2-chloro-3-(2-hydroxy-1-pyrrolidinyl)phenol,
2-chloro-3-(2-hydroxymethyl-1-pyrrolidinyl)phenol,
2-chloro-3-(2-methoxymethyl-1-pyrrolidinyl)phenol,
2-chloro-3-(3-carboxylic acid-1-pyrrolidinyl)phenol,
2-chloro-3-(3-carboxamide-1-pyrrolidinyl)phenol,
2-chloro-3-(3-hydroxy-1-pyrrolidinyl)phenol,
2-chloro-3-(3-hydroxymethyl-1-pyrrolidinyl)phenol,
2-chloro-3-(3-methoxymethyl-1-pyrrolidinyl)phenol,
2-fluoro-3-(2-carboxylic acid-1-pyrrolidinyl)phenol,
2-fluoro-3-(2-carboxamide-1-pyrrolidinyl)phenol,
2-fluoro-3-(2-hydroxy-1-pyrrolidinyl)phenol, 2-fluoro-3-(2-hydroxymethyl-1-pyrrolidinyl)phenol, 2-fluoro-3-(2-methoximethyl-1-pyrrolidinyl)phenol, 2-fluoro-3-(3-carboxylic acid-1-pyrrolidinyl)phenol, 2-fluoro-3-(3-carboxamide-1-pyrrolidinyl)phenol, 2-fluoro-3-(3-hydroxy-1-pyrrolidinyl)phenol, 2-fluoro-3-(3-hydroxymethyl-1-pyrrolidinyl)phenol, 2-fluoro-3-(3-methoxymethyl-1-pyrrolidinyl)phenol,
2-methoxy-3-(2-carboxylic acid-1-pyrrolidinyl)phenol,
2-methoxy-3-(2-carboxamide-1-pyrrolidinyl)phenol,
2-methoxy-3-(2-hydroxy-1-pyrrolidinyl)-phenol,
2-methoxy-3-(2-hydroxymethyl-1-pyrrolidinyl)phenol,
2-methoxy-3-(2-methoxymethyl-1-pyrrolidinyl)-phenol, 2-methoxy-3-(3-carboxylic acid-1-pyrrolidinyl)phenol, 2-methoxy-3-(3-carboxamide-1pyrrolidinyl)phenol,
2-methoxy-3-(3-hydroxy-1-pyrrolidinyl)phenol, 2-methoxy-3-(3-hydroxy-methyl-1-pyrrolidinyl)phenol, 2-methoxy-3-(3-methoxymethyl-1-pyrrolidinyl)phenol, 4-chloro-3-(2-carboxylic acid-1-pyrrolidinyl)phenol,
4-chloro-3-(2-carboxamide-1-pyrrolidinyl)phenol,
4-chloro-3-(2-hydroxy-1-pyrrolidinyl)phenol,4-chloro-3-(2-hydroxymethyl-1-pyrrolidinyl)phenol, 4-chloro-3-(2-methoxymethyl-1-pyrrolidinyl)phenol, 4-chloro-3-(3-carboxylic acid-1-pyrrolidinyl)phenol, 4-chloro-3-(3-carboxamide-1-pyrrolidinyl)phenol, 4-chloro-3-(3-hydroxy-1-pyrrolidinyl)phenol, 4-chloro-3-(3-hydroxymethyl-1-pyrrolidinyl)phenol,4-chloro-3-(3-methoxymethyl-1-pyrrolidinyl)phenol, 4-fluoro-3-(2-carboxylic acid-1-pyrrolidinyl)phenol,
4-fluoro-3-(2-carboxamide-1-pyrrolidinyl)phenol,
4-fluoro-3-(2-hydroxy-1-pyrrolidinyl)phenol, 4-fluoro-3-(2-hydroxymethyl-1-pyrrolidinyl)phenol,
4-fluoro-3-(2-methoxymethyl-1-pyrrolidinyl)phenol,
4-fluoro-3-(3-carboxylic acid-1-pyrrolidinyl)phenol,
4-fluoro-3-(3-carboxamide-1-pyrrolidinyl)phenol,
4-fluoro-3-(3-hydroxy-1-pyrrolidinyl)phenol, 4-fluoro-3-(3-hydroxymethyl-1-pyrrolidinyl)phenol, 4-fluoro-3-(3-methoxymethyl-1-pyrrolidinyl)phenol,
4-methoxy-3-(2-carboxylic acid-1-pyrrolidinyl)phenol, 4-methoxy-3-(2-carboxamide-1-pyrrolidinyl)-phenol, 4-methoxy-3-(2-hydroxy-1-pyrrolidinyl)phenol, 4-methoxy-3-(2-hydroxymethyl-1-pyrrolidinyl)phenol, 4-methoxy-3-(2-methoxymethyl-1-pyrrolidinyl)phenol, 4-methoxy-3-(3-carboxylic acid-1-pyrrolidinyl)phenol, 4-methoxy-3-(3-carboxamide-1-pyrrolidinyl)phenol,
4-methoxy-3-(3-hydroxy-1-pyrrolidinyl)phenol, 4-methoxy-3-(3-hydroxy-methyl-1-pyrrolidinyl)phenol, 4-methoxy-3-(3-methoxymethyl-1-pyrrolidinyl)phenol, 5-chloro-3-(2-carboxylic acid-1-pyrrolidinyl)phenol,
5-chloro-3-(2-carboxamide-1-pyrrolidinyl)phenol,
5-chloro-3-(2-hydroxy-1-pyrrolidinyl)phenol,
5-chloro-3-(2-hydroxymethyl-1-pyrrolidinyl)phenol,
5-chloro-3-(2-methoxymethyl-1-pyrrolidinyl)phenol,
5-chloro-3-(3-carboxylic acid-1-pyrrolidinyl)phenol,
5-chloro-3-(3-carboxamide-1-pyrrolidinyl)phenol,
5-chloro-3-(3-hydroxy-1-pyrrolidinyl)phenol,
5-chloro-3-(3-hydroxymethyl-1-pyrrolidinyl)phenol,
5-chloro-3-(3-methoxymethyl-1-pyrrolidinyl)phenol,
5-fluoro-3-(2-carboxylic acid-1-pyrrolidinyl)phenol,
5-fluoro-3-(2-carboxamide-1-pyrrolidinyl)phenol,
5-fluoro-3-(2-hydroxy-1-pyrrolidinyl)phenol, 5-fluoro-3-(2-hydroxymethyl-1-pyrrolidinyl)phenol,
5-fluoro-3-(2-methoxymethyl-1-pyrrolidinyl)phenol,
5-fluoro-3-(3-carboxylic acid-1-pyrrolidinyl)phenol,
5-fluoro-3-(3-carboxamide-1-pyrrolidinyl)phenol,
5-fluoro-3-(3-hydroxy-1-pyrrolidinyl)phenol,
5-fluoro-3-(3-hydroxymethyl-1-pyrrolidinyl)phenol,
5-fluoro-3-(3-methoxymethyl-1-pyrrolidinyl)phenol,
5-methoxy-3-(2-carboxylic acid-1-pyrrolidinyl)phenol,
5-methoxy-3-(2-carboxamide-1-pyrrolidinyl)phenol,
5-methoxy-3-(2-hydroxy-1-pyrrolidinyl)phenol,
5-methoxy-3-(2-hydroxymethyl-1-pyrrolidinyl)phenol,
5-methoxy-3-(2-methoxymethyl-1-pyrrolidinyl)phenol,
5-methoxy-3-(3-carboxylic acid-1-pyrrolidinyl)phenol,
5-methoxy-3-(3-carboxamide-1-pyrrolidinyl)phenol,
5-methoxy-3-(3-hydroxy-1-pyrrolidinyl)phenol,
5-methoxy-3-(3-hydroxymethyl-1-pyrrolidinyl)phenol,
5-methoxy-3-(3-methoxymethyl-1-pyrrolidinyl)phenol, 6-chloro-3-(2-carboxylic acid-1-pyrrolidinyl)phenol, 6-chloro-3-(2-carboxamide-1-pyrrolidinyl)phenol,
6-chloro-3-(2-hydroxy-1-pyrrolidinyl)phenol, 6-chloro-3-(2-hydroxymethyl-1-pyrrolidinyl)phenol, 6-chloro-3-(2-methoxymethyl-1-pyrrolidinyl)phenol, 6-chloro-3-(3-carboxylic acid-1-pyrrolidinyl)phenol, 6-chloro-3-(3-carboxamide-1-pyrrolidinyl)phenol, 6-chloro-3-(3-hydroxy-1-pyrrolidinyl)-phenol, 6-chloro-3-(3-hydroxymethyl-1-pyrrolidinyl)phenol, 6-chloro-3-(3-methoxymethyl-1-pyrrolidinyl)phenol, 6-fluoro-3-(2-carboxylic acid-1-pyrrolidinyl)phenol, 6-fluoro-3-(2-carboxamide-1-pyrrolidinyl)phenol, 6-fluoro-3-(2-hydroxy-1-pyrrolidinyl)phenol, 6-fluoro-3-(2-hydroxymethyl-1-pyrrolidinyl)phenol, 6-fluoro-3-(2-methoxymethyl-1-pyrrolidinyl)phenol,
6-fluoro-3-(3-carboxylic acid-1-pyrrolidinyl)phenol,
6-fluoro-3-(3-carboxamide-1-pyrrolidinyl)phenol,
6-fluoro-3-(3-hydroxy-1-pyrrolidinyl)-phenol,
6-fluoro-3-(3-hydroxymethyl-1-pyrrolidinyl)phenol,
6-fluoro-3-(3-methoxymethyl-1-pyrrolidinyl)phenol,
6-methoxy-3-(2-carboxylic acid-1-pyrrolidinyl)phenol,
6-methoxy-3-(2-carboxamide-1-pyrrolidinyl)phenol,
6-methoxy-3-(2-hydroxy-1-pyrrolidinyl)phenol, 6-methoxy-3-(2-hydroxy-methyl-1-pyrrolidinyl)phenol, 6-methoxy-3-(2-methoxymethyl-1-pyrrolidinyl)phenol, 6-methoxy-3-(3-carboxylic acid-1-pyrrolidinyl)phenol, 6-methoxy-3-(3-carboxamide-1-pyrrolidinyl)phenol, 6-methoxy-3-(3-hydroxy-1-pyrrolidinyl)phenol, 6-methoxy-3-(3-hydroxymethyl-1-pyrrolidinyl)phenol, 6-methoxy-3-(3-methoxymethyl-1-pyrrolidinyl)phenol, 2-(2-hydroxyethyl)-3-(2-(2-hydroxyethyl)-1-pyrrolidinyl)phenol, 2-(2-hydroxyethyl)-3-(2-carboxylic acid-1-pyrrolidinyl)phenol, 2-(2-hydroxyethyl)-3-(2-carboxamide-1-pyrrolidinyl)phenol, 2-(2-hydroxy-ethyl)-3-(2-hydroxy-1-pyrrolidinyl)phenol, 2-(2-hydroxyethyl)-3-(2-hydroxy-methyl-1-pyrrolidinyl)phenol, 2-(2-hydroxyethyl)-3-(2-methoxymethyl-1-pyrrolidinyl)phenol, 2-(2-hydroxyethyl)-3-(3-(2-hydroxyethyl)-1-pyrrolidinyl)phenol, 2-(2-hydroxyethyl)-3-(3-carboxylic acid-1-pyrrolidinyl)phenol, 2-(2-hydroxyethyl)-3-(3-carboxamide-1-pyrrolidinyl)phenol, 2-(2-hydroxy-ethyl)-3-(3-hydroxy-1-pyrrolidinyl)phenol, 2-(2-hydroxyethyl)-3-(3-hydroxy-methyl-1-pyrrolidinyl)phenol, 2-(2-hydroxyethyl)-3-(3-methoxymethyl-1-pyrrolidinyl)phenol, 2-ethyl-3-(2-(2-hydroxyethyl)-1-pyrrolidinyl)phenol, 2-ethyl-3-(2-carboxylic acid-1-pyrrolidinyl)phenol, 2-ethyl-3-(2-carboxamide-1-pyrrolidinyl)phenol, 2-ethyl-3-(2-hydroxy-1-pyrrolidinyl)-phenol 2-ethyl-3-(2-hydroxymethyl-1-pyrrolidinyl)phenol, 2-ethyl-3-(2-methoxymethyl-1-pyrrolidinyl)phenol, 2-ethyl-3-(3-(2-hydroxyethyl)-1-pyrrolidinyl)phenol, 2-ethyl-3-(3-carboxylic acid-1-pyrrolidinyl)phenol, 2-ethyl-3-(3-carboxamide-1-pyrrolidinyl)phenol, 2-ethyl-3-(3-hydroxy-1-pyrrolidinyl)phenol, 2-ethyl-3-(3-hydroxymethyl-1-pyrrolidinyl)phenol, 2-ethyl-3-(3-methoxymethyl-1-pyrrolidinyl)phenol, 2-methyl-3-(2-(2-hydroxyethyl)-1-pyrrolidinyl)phenol, 2-methyl-3-(2-carboxylic acid-1-pyrrolidinyl)phenol, 2-methyl-3-(2-carboxamide-1-pyrrolidinyl)phenol, 2-methyl-3-(2-hydroxy-1-pyrrolidinyl)phenol, 2-methyl-3-(2-hydroxymethyl-1-pyrrolidinyl)phenol, 2-methyl-3-(2-methoxymethyl-1-pyrrolidinyl)phenol, 2-methyl-3-(3-(2-hydroxyethyl)-1-pyrrolidinyl)phenol, 2-methyl-3-(3-carboxylic acid-1-pyrrolidinyl)phenol, 2-methyl -3-(3-carboxamide-1-pyrrolidinyl)phenol, 2-methyl-3-(3-hydroxy-1-pyrrolidinyl)phenol, 2-methyl-3-(3-hydroxymethyl-1-pyrrolidinyl)phenol, 2-methyl-3-(3-methoxymethyl-1-pyrrolidinyl)phenol, 2-trifluormethyl-3-(2-(2-hydroxyethyl)-1-pyrrolidinyl)-phenol, 2-trifluormethyl-3-(2-carboxylic acid-1-pyrrolidinyl)phenol, 2-trifluormethyl-3-(2-carboxamide-1-pyrrolidinyl)phenol, 2-trifluormethyl-3-(2-hydroxy-1-pyrrolidinyl)phenol, 2-trifluormethyl-3-(2-hydroxymethyl-1-pyrrolidinyl)phenol, 2-trifluormethyl-3-(2-methoxymethyl-1-pyrrolidinyl)-phenol, 2-trifluormethyl -3-(3-(2-hydroxyethyl)-1-pyrrolidinyl)phenol, 2-trifluormethyl-3-(3-carboxylic acid-1-pyrrolidinyl)phenol, 2-trifluormethyl-3-(3-carboxamide-1-pyrrolidinyl)phenol, 2-trifluormethyl -3-(3-hydroxy-1-pyrrolidinyl)phenol, 2-trifluormethyl-3-(3-hydroxymethyl-1-pyrrolidinyl)-phenol, 2-trifluormethyl-3-(3-methoxymethyl-1-pyrrolidinyl)phenol, 5-(2-hydroxyethyl)-3-(2-(2-hydroxyethyl)-1-pyrrolidinyl)phenol, 5-(2-hydroxyethyl)-3-(2-carboxylic acid-1-pyrrolidinyl)phenol, 5-(2-hydroxy-ethyl)-3-(2-carboxamide-1-pyrrolidinyl)phenol, 5-(2-hydroxyethyl)-3-(2-hydroxy-1-pyrrolidinyl)phenol, 5-(2-hydroxyethyl)-3-(2-hydroxymethyl-1-pyrrolidinyl)phenol, 5-(2-hydroxyethyl )-3-(2-methoxymethyl-1-pyrrolidinyl)-phenol, 5-(2-hydroxyethyl)-3-(3-(2-hydroxyethyl)-1-pyrrolidinyl )phenol, 5-(2-hydroxyethyl )-3-(3-carboxylic acid-1-pyrrolidinyl)phenol, 5-(2-hydroxy-ethyl)-3-(3-carboxamide-1-pyrrolidinyl)phenol, 5-(2-hydroxyethyl)-3-(3-hydroxy-1-pyrrolidinyl)phenol, 5-(2-hydroxyethyl)-3-(3-hydroxymethyl-1-pyrrolidinyl)phenol, 5-(2-hydroxyethyl)-3-(3-methoxymethyl-1-pyrrolidinyl)-phenol, 5-ethyl-3-(2-(2-hydroxyethyl)-1-pyrrolidinyl)phenol, 5-ethyl-3-(2-carboxylic acid-1-pyrrolidinyl)phenol, 5-ethyl-3-(2-carboxamide-1-pyrrolidinyl)phenol, 5-ethyl-3-(2-hydroxy-1-pyrrolidinyl)phenol, 5-ethyl-3-(2-hydroxymethyl-1-pyrrolidinyl)phenol, 5-ethyl-3-(2-methoxymethyl-1-pyrrolidinyl)phenol, 5-ethyl-3-(3-(2-hydroxyethyl)-1-pyrrolidinyl)phenol, 5-ethyl-3-(3-carboxylic acid-1-pyrrolidinyl)phenol, 5-ethyl-3-(3-carboxamide-1-pyrrolidinyl)phenol, 5-ethyl-3-(3-hydroxy-1-pyrrolidinyl)-phenol, 5-ethyl-3-(3-hydroxymethyl-1-pyrrolidinyl)phenol, 5-ethyl-3-(3-methoxymethyl-1-pyrrolidinyl)phenol, 5-methyl-3-(2-(2-hydroxyethyl)-1-pyrrolidinyl)phenol, 5-methyl-3-(2-carboxylic acid-1-pyrrolidinyl)phenol, 5-methyl-3-(2-carboxamide-1-pyrrolidinyl)phenol, 5-methyl-3-(2-hydroxy-1-pyrrolidinyl)phenol, 5-methyl-3-(2-hydroxymethyl-1-pyrrolidinyl)phenol, 5-methyl-3-(2-methoxymethyl-1-pyrrolidinyl)phenol, 5-methyl-3-(3-(2-hydroxyethyl)-1-pyrrolidinyl)phenol, 5-methyl-3-(3-carboxylic acid-1-pyrrolidinyl)phenol, 5-methyl-3-(3-carboxamide-1-pyrrolidinyl)phenol, 5-methyl-3-(3-hydroxy-1-pyrrolidinyl)phenol, 5-methyl-3-(3-hydroxymethyl-1-pyrrolidinyl)phenol, 5-methyl-3-(3-methoxymethyl-1-pyrrolidinyl)phenol, 5-trifluormethyl-3-(2-(2-hydroxyethyl)-1-pyrrolidinyl)-phenol, 5-trifluormethyl-3-(2-carboxylic acid-1-pyrrolidinyl)phenol, 5-trifluormethyl-3-(2-carboxamide-1-pyrrolidinyl)phenol, 5-trifluormethyl-3-(2-hydroxy-1-pyrrolidinyl)phenol, 5-trifluormethyl-3-(2-hydroxymethyl-1-pyrrolidinyl)-phenol, 5-trifluormethyl-3-(2-methoxymethyl-1-pyrrolidinyl)-phenol, 5-trifluormethyl-3-(3-(2-hydroxyethyl)-1-pyrrolidinyl)phenol, 5-trifluormethyl-3-(3-carboxylic acid-1-pyrrolidinyl)phenol, 5-trifluormethyl-3-(3-carboxamide-1-pyrrolidinyl)phenol, 5-trifluormethyl-3-(3-hydroxy-1-pyrrolidinyl)phenol, 5-trifluormethyl-3-(3-hydroxymethyl-1-pyrrolidinyl)-phenol, 5-trifluormethyl-3-(3-methoxymethyl-1-pyrrolidinyl)phenol, 6-(2-hydroxymethyl)-3-(2-(2-hydroxyethyl)-1-pyrrolidinyl)phenol, 6-(2-hydroxyethyl)-3-(2-carboxylic acid-1-pyrrolidinyl)phenol, 6-(2-hydroxy-ethyl)-3-(2-carboxamide-1-pyrrolidinyl)phenol, 6-(2-hydroxyethyl)-3-(2-hydroxy-1-pyrrolidinyl)phenol, 6-(2-hydroxyethyl)-3-(2-hydroxymethyl-1-pyrrolidinyl)phenol, 6-(2-hydroxyethyl)-3-(2-methoxymethyl-1-pyrrolidinyl)-phenol, 6-(2-hydroxyethyl)-3-(3-(2-hydroxyethyl)-1-pyrrolidinyl)phenol, 6-(2-hydroxyethyl)-3-(3-carboxylic acid-1-pyrrolidinyl)phenol, 6-(2-hydroxy-ethyl)-3-(3-carboxamide-1-pyrrolidinyl)phenol, 6-(2-hydroxyethyl)-3-(3-hydroxy-1-pyrrolidinyl)phenol, 6-(2-hydroxyethyl)-3-(3-hydroxymethyl-1-pyrrolidinyl)phenol, 6-(2-hydroxyethyl)-3-(3-methoxymethyl-1-pyrrolidinyl)-phenol, 6-ethyl-3-(2-(2-hydroxyethyl)-1-pyrrolidinyl)phenol, 6-ethyl-3-(2-carboxylic acid-1-pyrrolidinyl)

phenol, 6-ethyl-3-(2-carboxamide-1-pyrrolidinyl)phenol, 6-ethyl-3-(2-hydroxy-1-pyrrolidinyl)phenol, 6-ethyl-3-(2-hydroxymethyl-1-pyrrolidinyl)phenol, 6-ethyl-3-(2-methoxymethyl-1-pyrrolidinyl)phenol, 6-ethyl-3-(3-(2-hydroxyethyl)-1-pyrrolidinyl)phenol,
6-ethyl-3-(3-carboxylic acid-1-pyrrolidinyl)phenol, 6-ethyl-3-(3-carboxamide-1-pyrrolidinyl)phenol, 6-ethyl-3-(3-hydroxy-1-pyrrolidinyl)-phenol, 6-ethyl-3-(3-hydroxymethyl-1-pyrrolidinyl)phenol, 6-ethyl-3-(3-methoxymethyl-1-pyrrolidinyl)phenol, 6-methyl-3-(2-(2-hydroxyethyl)-1-pyrrolidinyl)phenol, 6-methyl-3-(2-carboxylic acid-1-pyrrolidinyl)phenol,
6-methyl-3-(2-carboxamide-1-pyrrolidinyl)phenol, 6-methyl-3-(2-hydroxy-1-pyrrolidinyl)phenol, 6-methyl-3-(2-hydroxymethyl-1-pyrrolidinyl)phenol,
6-methyl-3-(2-methoxymethyl-1-pyrrolidinyl)phenol, 6-methyl-3-(3-(2-hydroxyethyl)-1-pyrrolidinyl)phenol, 6-methyl-3-(3-carboxylic acid-1-pyrrolidinyl)phenol, 6-methyl-3-(3-carboxamide-1-pyrrolidinyl)phenol,
6-methyl-3-(3-hydroxy-1-pyrrolidinyl)phenol, 6-methyl-3-(3-hydroxymethyl-1-pyrrolidinyl)phenol, 6-methyl-3-(3-methoxymethyl-1-pyrrolidinyl)phenol, 6-trifluormethyl-3-(2-(2-hydroxyethyl)-1-pyrrolidinyl)phenol, 6-trifluormethyl-3-(2-carboxylic acid-1-pyrrolidinyl)phenol, 6-trifluormethyl-3-(2-carboxamide-1-pyrrolidinyl)phenol, 6-trifluormethyl-3-(2-hydroxy-1-pyrrolidinyl)phenol, 6-trifluormethyl-3-(2-hydroxymethyl-1-pyrrolidinyl)-phenol, 6-trifluormethyl-3-(2-methoxymethyl-1-pyrrolidinyl)phenol,
6-trifluormethyl-3-(3-(2-hydroxyethyl)-1-pyrrolidinyl) phenol, 6-trifluormethyl-3-(3-carboxylic acid-1-pyrrolidinyl)phenol, 6-trifluormethyl-3-(3-carboxamide-1-pyrrolidinyl)phenol, 6-trifluormethyl-3-(3-hydroxy-1-pyrrolidinyl)phenol, 6-trifluormethyl-3-(3-hydroxymethyl-1-pyrrolidinyl)-phenol and 6-trifluormethyl -3-(3-methoxymethyl-1-pyrrolidinyl) phenol, or the physiologically tolerated salts thereof.

4. An agent according to claim 1, comprising the meta-aminophenol derivative of formula (I) in an amount of from 0.005% to 20% by weight.

5. An agent according to claim 1, wherein the developer substance is selected from the group consisting of 1,4-diaminobenzene, 1,4-diamino-2-methylbenzene, 1,4-diamino-2,6-dimethylbenzene, 1,4-diamino-3,5-diethylbenzene, 1,4-diamino-2,5-di-methylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 4-(2,5-diaminophenyl)-2-((diethylamino)methyl)thiophene, 2-chloro-3-(2,5-diaminophenyl)thiophene, 1,4-diamino-2-(pyridin-3-yl) benzene, 2,5-diaminobiphenyl, 2,5-diamino-4'-(1-methylethyl)-1,1'-biphenyl, 2,3',5-triamino-1,1'-biphenyl, 1,4-diamino-2-methoxymethylbenzene, 1,4-diamino-2-aminomethylbenzene, 1,4-diamino-2-((phenylamino)methyl) benzene, 1,4-diamino-2-((ethyl-(2-hydroxyethyl)-amino) methyl)benzene, 1,4-diamino-2-hydroxymethyl-benzene, 1,4-diamino-2-(2-hydroxyethoxy)benzene, 2-(2-(acetylamino)-ethoxy)-1,4-diaminobenzene, 4-phenylaminoaniline, 4-dimethylamino-aniline, 4-diethylaminoaniline, 4-dipropylaminoaniline, 4-[ethyl(2-hydroxyethyl)-amino] aniline, 4-[di(2-hydroxy-ethyl)amino]aniline, 4-[di(2-hydroxyethyl)-amino]-2-methylaniline, 4-[(2-methoxyethyl) amino]aniline, 4-[(3-hydroxy-propyl)amio]aniline, 4-[(2,3-dihydroxy-propyl)amino]aniline, 4-(((4-aminophenyl)methyl)amino)aniline, 4-[(4-aminophenylamino)-methyl]phenol, 1,4-diamino-N-(4-pyrrolidin-1-yl-benzyl)benzene, 1,3-dihydroxy-2-((2-furylmethyl)aminomethyl)benzene, 1,4-diamino-N-thiophen-2-ylmethylbenzene 1,4-diamino-N-furan-2-ylmethylbenzene, 1,4-diamino-N-thiophen-3-ylmethylbenzene, 1,4-diamino-N-benzyl benzene, 1,4-diamino-2-(1-hydroxyethyl)benzene, 1,4-diamino-2-(2-hydroxyethyl)-benzene, 1,4-diamino-2-(1-methylethyl)benzene, 1,3-bis[(4-aminophenyl)-(2-hydroxyethyl)amino]-2-propanol, 1,4-bis[(4-aminophenyl)amino]butane, 1,8-bis(2,5-diaminophenoxy)-3,6-dioxaoctane, 2,5-diamino-4'-hydroxy-1,1'-biphenyl, 2,5-diamino-2'-trifluoromethyl-1,1'-biphenyl, 2,4',5-triamino-1,1'-biphenyl, 4-aminophenol, 4-amino-3-methyl phenol, 4-amino-3-(hydroxymethyl)phenol, 4-amino-3-fluorophenol, 4-methylaminophenol,
4-amino-2-(aminomethyl)phenol, 4-amino-2-(hydroxymethyl)phenol,
4-amino-2-fluorophenol, 4-amino-2-[(2-hydroxyethyl) amino]methylphenol, 4-amino-2-methylphenol, 4-amino-2-(methoxymethyl)phenol, 4-amino-2-(2-hydroxyethyl)phenol, 5-aminosalicylic acid, 2,5-diaminopyridine, 2,4,5,6-tetraaminopyrimidine, 2,5,6-triamino-4-(1H)-pyrimidone,
4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole,
4,5-diamino-1-methyl-1H-pyrazole, 4,5-diamino-1-pentyl-1H-pyrazole,
4,5-diamino-1-(phenylmethyl)-1H-pyrazole, 4,5-diamino-1-((4-methoxyphenyl)methyl-1H-pyrazole, 2-aminophenol, 2-amino-6-methylphenol, 2-amino-5-methylphenol, 1,2,4-trihydroxybenzene,
2,4-diaminophenol, 1,4-dihydroxybenzene and 2-(((4-aminophenyl)-amino)methyl)-1,4-diaminobenzene.

6. An agent according to claim 1, further comprising at least one additional coupler substance and/or at least one direct dye.

7. An agent according to claim 1, wherein the developer substances and coupler substances, based on the total amount of the colorant, are present in each case in a total amount of from 0.005% to 20% by weight.

8. An agent according to claim 1, wherein the agent is a hair dye.

* * * * *